United States Patent

Aaronson et al.

Patent Number: 5,183,905
Date of Patent: Feb. 2, 1993

[54] PHENOLPHTHALEIN BIS (DIHYDROCARBYL PHOSPHATE) COMPOUNDS

[75] Inventors: Alan M. Aaronson, Flushing Meadows; Danielle A. Bright, Spring Valley, both of N.Y.

[73] Assignee: Akzo NV, Arnhem, Netherlands

[21] Appl. No.: 870,748

[22] Filed: Apr. 20, 1992

Related U.S. Application Data

[63] Continuation of Ser. No. 660,452, Feb. 25, 1991, abandoned.

[51] Int. Cl.$^5$ .................... C07F 9/06; C09K 21/00
[52] U.S. Cl. ........................ 549/218; 252/609; 252/608
[58] Field of Search ............. 549/218; 252/609, 608

[56] References Cited

U.S. PATENT DOCUMENTS

| | | | |
|---|---|---|---|
| 4,057,532 | 11/1977 | Saferstein et al. | 260/47 |
| 4,134,936 | 1/1979 | Byrne et al. | 260/860 |
| 4,167,536 | 9/1979 | Factor | 525/450 |
| 4,343,732 | 8/1982 | Zama et al. | 524/114 |

FOREIGN PATENT DOCUMENTS 88928 8/1974 Japan.
55947 4/1982 Japan.

OTHER PUBLICATIONS

Adeka Argus Chemical Co. Ltd. CA 97-128624b (1982).

*Primary Examiner*—Cecilia Tsang
*Attorney, Agent, or Firm*—Richard P. Fennelly; Louis A. Morris

[57] ABSTRACT

Phenolphthalein bis(dihydrocarbyl phosphates), optionally substituted with chloro or bromo atoms, can be used as fire retardant additives for polymers.

8 Claims, No Drawings

PHENOLPHTHALEIN BIS (DIHYDROCARBYL PHOSPHATE) COMPOUNDS

This is a continuation of application Ser. No. 660,452 filed Feb. 25, 1991, now abandoned.

BACKGROUND OF THE INVENTION

A variety of bis(dihydrocarbyl phosphate) compounds are known to persons of ordinary skill in the art who might be interested, for example, in using such organophosphorus compounds as flame retardants for polymers. Examples of bis(hydrocarbyl phosphate) compounds which contain various types of bridging groups between the two phosphate moieties can be found by consulting the following: Japanese Kokai No. 10 74/40,342 (aliphatic divalent groups which can contain an ether bond); U.S. Pat. No. 3,869,526 (aliphatic straight, branched or cyclic organic alkylene residues or a hydrocarbon ether residue); Japanese Kokai No. 82/174,331 (phenyl, bisphenol A-derived, biphenyl, etc.); U.S. Pat. No. 4,343,732 (a residue of a polyhydric alcohol or phenol or of a polyoxyalkylene glycol).

Japanese Kokai No. 82/55,947 depicts a rather wide variety of bisphosphate compounds with differing bridging groups including those containing multiple phenyl rings in the bridging group but not one containing a nucleus derived from phenolphthalein, also termed "3,3-bis(4-hydroxyphenyl)-1(3H)-isobenzofuranone".

Copending applications which describe certain bis(-dihydrocarbyl phosphates) include: U.S. Ser. No. 374,716, filed Jul. 3, 1989 and U.S Ser. No. 374,718, filed Jul. 3, 1989.

The use of phenolphthalein-based polymers, as contrasted to monomeric bis(hydrocarbyl phosphates), as flame retardants is disclosed in the following three literature references: J. Polym. Sci., Chem. Ed., Vol. 19, pages 2151, 2659, and 2773 (1981). In addition, the following patent documents indicate the flame retardant characteristics for a variety of phenolphthalein-containing polymers. U.S. Pat. Nos. 4,057,532 (phenolphthalein polyesters); 4,134,936 (copolycarbonates of phenolphthalein polycarbonates and other polycarbonates); and 4,167,536 (organopolysiloxanephenolphthalein-polycarbonate copolymers).

Japanese Kokai No. 74/88,928 describes fire resistant thermoplastic compositions which contain a phosphate, phosphonate, phosphite or phosphinate polyester (a polymeric additive also) of phenolphthalein containing bromine or chlorine substituents on the rings.

DESCRIPTION OF THE INVENTION

The instant invention relates to novel phenolphthalein bis(hydrocarbyl phosphate) compounds, as contrasted to polymers, and to flame retarded polymer compositions containing them, for example, either thermoplastic or thermoset polymers. The compounds of the instant invention have the general formula

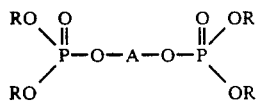

where —O—A—O— is a phenolphthalein moiety (minus the hydroxy hydrogen atoms), and R is hydrocarbyl, such as $C_1$-$C_{20}$ alkyl, cycloalkyl, allyl, $C_2$-$C_b$ alkenyl, or aryl (e.g., phenyl, 2-xylenyl, cresyl, naphthyl, xenyl, isopropylphenyl, and t-butylphenyl). If desired, R and A can both be substituted with such atoms as chloro or bromo. For example, 2,4-dibromophenyl and 2,4,6-tribromophenyl are representative R groups when halogenated phenyl groups are desired.

The compounds can be formed by reaction of an alkali metal salt of phenolphthalein with at least twice the stoichiometric amount of the appropriate dihydrocarbylhalophosphate under phase transfer conditions.

The following Examples illustrate various embodiments of the instant invention.

EXAMPLE 1

To a two liter, three-necked flask equipped with a mechanical stirrer, dropping funnel and thermometer was added 500 ml of water and 40 gm (1.0 mole) of sodium hydroxide while stirring. Phenolphthalein (159 gm, 0.50 mole) was added portionwise in such a manner to keep the temperature below 40° C. The reaction mixture was purple. After cooling to 25° C., 750 ml of methylene chloride and 5 gm of tricaprylyl methyl ammonium chloride (ALIQUAT 336 brand) were added to the reaction mixture. Then, 336 gm (1.25 moles) of diphenyl chlorophosphate were added dropwise at 20°-25° C. over one and one-half hours while maintaining good stirring. When the addition was completed, the purple color was replaced by a very light pink color. The reaction mixture was stirred overnight at room temperature and lost the pink color. The two layers were separated. The organic layer was washed with 3×500 ml of 2% sodium hydroxide solution followed by 500 ml of water. The solvent was removed under vacuum to give 326.3 gm of a very viscous yellow oil which assayed at 97% by liquid chromatography (LC). The anticipated structure, tetraphenyl phenolphthalein diphosphate, was confirmed by $^{31}$P NMR.

EXAMPLE 2

To a 500 ml three-necked flask equipped with mechanical stirrer, dropping funnel and thermometer, there was added 100 ml of Water and 6.36 gm (0.159 mole) of sodium hydroxide while stirring. Tetrabromophenolphthalein (50 gm, 0.0789 mole) was added portionwise in such a way to keep the temperature below 40° C. The reaction mixture was purple.

After cooling to 25° C., 200 ml of methylene chloride and 0.2 gm of ALIQUAT 336 brand product were added to the reaction mixture. Then 41.2 gm (0.159 mole) of diphenyl chlorophosphate was added dropwise at 20°-25° C. over 35 minutes while maintaining good stirring. When the addition was completed, the reaction mixture was still purple. The reaction mixture was stirred overnight at room temperature and turned light yellow.

The two layers were separated. The organic layer was washed with 2×200 ml of 2% sodium hydroxide solution followed by 3×200 ml of water. The solvent was removed under vacuum to give 57.6 gm of a very viscous yellow oil that solidified and assayed at 96% by LC as tetrabromophenolphthalein bis(diphenylphosphate).

EXAMPLE 3

Nylon 6 was mixed with 10% silica (SILTEX brand) to prevent dripping of the formulation when tested as described below, and was then tested with no fire retardant additive and with an additional 10% of the compound of Example 1. The Limiting Oxygen Index (LOI) values obtain are as follows:

| Additive | LOI |
|---|---|
| None | 23.0 |
| Ex. 1 Cpd - 10% | 25.6 |

EXAMPLES 4-5

The following flame retardancy tests of tetraphenyl phenolphthalein diphosphate, from Example 1, were undertaken in nylon 6 using inorganic drip retarders and carriers in view of the propensity of nylon 6 to drip when burned.

The formulation used in Example 4 comprised 70% nylon 6, 10% of the diphosphate, 5% of finely divided hydrated synthetic calcium silicate (MICRO-CEL E brand), as a carrier for the diphosphate, and 15% of fused silica powder (SILTEX 32 brand). The flammability results were: 30.8 LOI; UL 94 burned with a flaming drip and had a burning time in excess of that for U2.

The formulation used in Example 5 comprised 70% nylon 6, 20% of the diphosphate, and 10% of the calcium silicate carrier used above. The flammability results were better than for Example 4: 32.0 LOI; UL 94 —almost a V1 rating with an average burn time of 26.8 seconds and a longest burn time of 41 seconds (V1 requires an average burn time of not over 25 seconds with a longest burn time of 30 seconds).

The foregoing Examples illustrate only certain embodiments of the present invention and, for that reason, should not be construed in a limiting sense. The scope of protection sought is set forth in the claims which follow.

We claim:

1. A phenolphthalein bis(dihydrocarbyl phosphate) compound of the formula

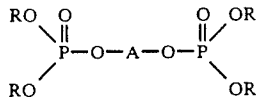

where R is selected from the group consisting of $C_1$-$C_{20}$ alkyl, cycloalkyl, $C_2$-$C_{12}$ alkenyl, and phenyl and —O—A—O— is a phenolphthalein moiety minus its hydroxy hydrogen atoms.

2. A compound as claimed in claim 1 where R is phenyl.

3. A compound as claimed in claim 1 where R contains a substituent selected from the group consisting of chloro and bromo.

4. A compound as claimed in claim 1 where R is a halogenated phenyl group.

5. A polymer composition containing the compound of claim 1 as a flame retardant.

6. A polymer composition containing the compound of claim 2 as a flame retardant.

7. A polymer composition containing the compound of claim 3 as a flame retardant.

8. A polymer composition containing the compound of claim 4 as a flame retardant.

* * * * *